United States Patent [19]

Ebbers et al.

[11] Patent Number: 5,164,482
[45] Date of Patent: Nov. 17, 1992

[54] RECOMBINANT APROTININ VARIANTS GENETICALLY ENGINEERED PROCESS FOR THE MICROBIAL PREPARATION OF HOMOGENEOUSLY PROCESSED APROTININ VARIANTS AND THE THERAPEUTIC USE THEREOF

[75] Inventors: Jürgen Ebbers; Dietrich Hörlein; Michael Schedel; Rathindra Das, all of Wuppertal-Elberfeld, Fed. Rep. of Germany

[73] Assignee: Bayer Aktiengesellschaft, Leverkusen, Fed. Rep. of Germany

[21] Appl. No.: 573,521

[22] Filed: Aug. 24, 1990

[30] Foreign Application Priority Data

Sep. 13, 1989 [DE] Fed. Rep. of Germany ....... 3930522

[51] Int. Cl.⁵ .................... C07K 15/04; C07K 15/06; C07K 7/10
[52] U.S. Cl. ..................................... 530/324; 514/12; 435/69.1; 435/69.2; 435/172.1
[58] Field of Search ................... 405/172.1, 69.2, 69.1; 530/324; 514/12

[56] References Cited

U.S. PATENT DOCUMENTS 5,037,806  8/1991  Krivi ................................. 530/399

FOREIGN PATENT DOCUMENTS 339942   11/1989  European Pat. Off. .
8901968  3/1989   PCT Int'l Appl. .
2188322  9/1987   United Kingdom .

Primary Examiner—Howard E. Schain
Attorney, Agent, or Firm—Sprung Horn Kramer & Woods

[57] ABSTRACT

An aprotinin with a deletion of the amino acid proline in position 2 or an addition of alanine-(-2)- glutamine-(-1). Such aprotinin is useful as an active ingredient in medicaments.

5 Claims, 10 Drawing Sheets

```
        HindIII                                    XhoI
    AAGCTTGGATAAAAGAGACGTCCGGACTTCTGCCTCGAGCCGCCCGTACACTGGGCCCTGCGT
1   ----+----+----+----+----+----+----+----+----+----+----+----+  +60
    TTCGAACCTATTTTCTGCAGGCCTGAAGACGGAGCTCGGGGCATGTGACCCGGGACGCA
    Ser Leu Asp Lys Arg Arg Pro Asp Phe Cys Leu Glu Pro Pro Tyr Thr Gly Pro Cys Val
    ────────α-F-Leader──────────┤
                            KEX2
                                                  StuI
    TGCTTTGATCATCCGTTACTTTCTACAATGCAAAGGCAGGCCTGTGTCAGACCTTCGTATA
61  ----+----+----+----+----+----+----+----+----+----+----+----+  +120
    ACGAAACTAGTAGGCAATGAAGATGTTACGTTTCCGTCCGGACACAGTCTGGAAGCATAT
    Ala Leu Ile Ile Arg Tyr Phe Tyr Asn Ala Lys Ala Gly Leu Cys Gln Thr Phe Val Tyr PstI                                        SacII                      SphI
    CGGCGGGCTGCAGAGCTAAGCGTAACAACTTCAAATCCGGGAAGACTGCATGCGTACTTG
121 ----+----+----+----+----+----+----+----+----+----+----+----+  +180
    GCCGCCCGACGTCTCGATTCGCATTGTTGAAGTTTAGGCGCCTTCTGACGTACGCATGAAC
    Gly Gly Cys Arg Ala Lys Arg Asn Asn Phe Lys Ser Ala Glu Asp Cys Met Arg Thr Cys BamHI
    CGGTGGGTGCTTAGGCAAGCTCGGGATCC
181 ----+----+----+----+----+----  208
    GCCACCACGAATCCGTTCGAGCCCTAGG
    Gly Gly Ala End
```

FIG. 4

| Amino acid | Ala-(-2)-Gln-(-1)-Val-15-Leu-17-Aprotinin | DesPro-2,Arg-15 Aprotinin | Ala-(-2)-Gln-(-1)-Arg-15-Aprotinin | Aprotinin |
|---|---|---|---|---|
| Asx | 5.2 (5) | 5.1 (5) | 5.1 (5) | 5 |
| Thr | 2.8 (3) | 2.7 (3) | 2.8 (3) | 3 |
| Ser | 0.9 (1) | 1.0 (1) | 0.9 (1) | 1 |
| Glx | 4.0 (4) | 3.1 (3) | 3.9 (4) | 3 |
| Pro | n.b. | n.b. | n.b. | 4 |
| Gly | 6.1 (6) | 6.2 (6) | 6.1 (6) | 6 |
| Ala | 7.0 (7) | 6.0 (6) | 7.0 (7) | 6 |
| Cys | n.b. | n.b. | n.b. | 6 |
| Val | 1.9 (2) | 0.9 (1) | 0.8 (1) | 1 |
| Met | 0.9 (1) | 0.9 (1) | 0.9 (1) | 1 |
| Ile | 1.7 (2) | 1.6 (2) | 1.7 (2) | 2 |
| Leu | 3.1 (3) | 2.0 (2) | 2.1 (2) | 2 |
| Tyr | 3.9 (4) | 4.1 (4) | 3.9 (4) | 4 |
| Phe | 4.1 (4) | 4.2 (4) | 4.0 (4) | 4 |
| Lys | 3.2 (3) | 3.1 (3) | 3.1 (3) | 4 |
| Arg | 5.1 (5) | 7.1 (7) | 6.9 (7) | 6 |

FIG.7

| | -2 -1 1 2 3 4 5 6 7 8 9 10 11 12 13 14 15 16 17 |
|---|---|
| Ala-(-2)-Gln-(-1)-Val-15-Leu-17-Aprotinin | A-Q*-R-P-D-F-C-L-E-P-P-Y-T-G-P-C-Y-A-L |
| DesPro-2-Arg-15-Aprotinin | R—D-F-C-L-E-P-P-Y-T-G-P-C-R-A-R |
| Ala-(-2)-Gln-(-1)-Arg-15-Aprotinin | A-Q*-R-P-D-F-C-L-E-P-P-Y-T-G-P-C-R-A-R |

\* The glutamine may be partially deamiated during the purification

FIG. 8

| Aprotinin-variant | % Correct processing |
|---|---|
| DesPro-2-Val-15- | ~70 – 75 |
| DesPro-2-Val-15-Leu-17- | ~70 – 75 |
| DesPro-2-Arg-15 | ~70 |
| Ala-(-2)-Gln-(-1)-Arg-15- | ~80 – 90 |
| Ala-(-2)-Gln-(-1)-Val-15-Leu-17- | ~80 – 90 |
| Val-15-Leu-17- | 0 |

FIG.9

| Variant | Inhibition of HLE | | Inhibition of porcine pancreas Kallikrein |
|---|---|---|---|
| | $K_i$ (molar) | $k_{on}$ ($M^{-1} \times sec^{-1}$) | $K_i$ (molar) |
| DePro-2-Val-15- | $2 \times 10^{-10}$ | $1-2 \times 10^{5}$ | |
| DePro-2-Val-15-Leu-17- | $2-4 \times 10^{-11}$ | $1-3 \times 10^{6}$ | |
| DePro-2-Val-15-Leu-17-Arg-19- | $4 \times 10^{-11}$ | $2 \times 10^{6}$ | |
| DePro-2-Val-15-Leu-17-Glu-52- | $2-4 \times 10^{-11}$ | $1-3 \times 10^{6}$ | |
| Ala-(-2)-Gln-(-1)-Val-15-Leu-17- | $2-4 \times 10^{-11}$ | $1-3 \times 10^{6}$ | |
| Ala-(-2)-Gln-(-1)-Val-15-Leu-17-Arg-19- | $3-5 \times 10^{-11}$ | $1-3 \times 10^{6}$ | |
| Val-15-Leu-17-Glu-52- [1] | $2-6 \times 10^{-11}$ | $1-3 \times 10^{6}$ | |
| DePro-2-Arg-15- | | | $2-3 \times 10^{-10}$ |
| DePro-2-Arg-15-Ala-17- | | | $7-9 \times 10^{-11}$ |
| Ala-(-2)-Gln-(-1)-Arg-15- | | | $1.5-3 \times 10^{-10}$ |
| DePro-2- | | | $5-7 \times 10^{-10}$ |
| Aprotinin | | | $5-7 \times 10^{-10}$ |

FIG. 10

[1] Comparison substance; isolated from E. coli

RECOMBINANT APROTININ VARIANTS GENETICALLY ENGINEERED PROCESS FOR THE MICROBIAL PREPARATION OF HOMOGENEOUSLY PROCESSED APROTININ VARIANTS AND THE THERAPEUTIC USE THEREOF

BACKGROUND OF THE INVENTION

1. Field of the Invention

The present invention relates to recombinant aprotinin variants; processes to prepare the described peptide variants as homogeneously processed secretion products with transformed yeasts, and medicaments containing the recombinant aprotinin variants.

2. Background Information

Aprotinin is a well-investigated protein which contains 58 amino acids and acts to inhibit trypsin, chymotrypsin, plasmin and plasma kallikrein (H. Fritz and G. Wunderer, Drug. Res. 33, 479–494, 1983; W. Gebhard, H. Tschesche and H. Fritz, Proteinase Inhibitors, Barrett and Salvesen (eds.), Elsevier Science Publ. BV 375–387, 1986).

Aprotinin obtained from bovine organs is the active substance in the medicament Trasylol ® which is used for the treatment of various disorders such as, for example, hyperfibrinolytic hemorrhages and traumat.-hemorrhagic shock.

In addition, there are new clinical findings which show that the blood loss caused by fibrinolysis and coagulation in open-heart surgery can be considerably reduced by use of Trasylol ® (W. van Oeveren et al. Ann. Thorac. Surg. 44, 640–645, 1987; D. Royston et al. Lancet II, 1289–1291, 1987; B. P. Bistrup et al., Lancet I, 366–367, 1988).

It has been possible to show that semisynthetically generated homologues of aprotinin which contain other amino acids in place of lysine in position 15 of the amino acid sequence have a profile of action and specificity of action which differ distinctly from those of aprotinin (Tschesche et al., U.S. Pat. No. 4,595,674; H. R. Wenzel et al. in Chemistry of Peptides and Proteins, Volume 3, 1985).

Some of these semisynthetic aprotinin homologues have, for example, a strongly inhibiting action on elastase from pancreas and leucocytes. Owing to this novel specificity of action, these aprotinin homologues can be used therapeutically for disorders caused by an increased release of elastase, such as, for example, development of emphysema, ARDS (adult respiratory distress syndrome) and rheumatoid arthritis.

Other aprotinin homologues with arginine in position 15 are characterized by an inhibititory action which is distinctly greater than that of aprotinin on plasma kallikrein, which is centrally involved in the blood coagulation cascade.

Experience has shown that the yields achievable by semisynthetic modification of bovine aprotinin are small. It was therefore desirable to prepare by fermentation recombinant (rec.) gene products in prokaryotic microorganisms for the preparation of large amounts of aprotinin homologues advantageously using synthetically prepared genes (Auerswald et al., Patent EP 01238993 A2; B. V. Wilcken-Bergmann et al., EMBO J. 5, 3219–3225, 1986).

For example, the expression systems used for the preparation of rec. aprotinin variants in E. coli K 12 strains were ones which accumulate, in the form of intracellular inclusion bodies, the aprotinin mutein as a fusion protein, which is formed within the cell, with a suitable fusion partner such as, for example, the N-terminal peptide portion of MS 2 replicase (E. A. Auerswald et al., Biol. Chem. Hoppe Seyler 369, 27–35, 1988)

Besides these, it is also possible to use E. coli expression/secretion systems which make possible, by fusion of the aprotinin mutein with suitable gene sequences for secretory signal peptides, such as, for example, the OmpA signal sequence or the phoA signal sequence, the secretion of inhibitory aprotinin variants into the periplasm of the bacterial cell (personal communication, Dr. W. Bruns—Bayer AG; C. B. Marks et al., J. Biol. Chem. 261, 7115–7118, 1986).

Among eukaryotic systems, yeast expression systems are particularly suitable for the genetically engineered preparation of rec. aprotinin variants, in which the gene product is either accumulated within the cell or, as fusion with a suitable secretory signal sequence from yeasts, passed through the secretion pathway and, after cleavage off by a membrane protease, exported as inhibitory substance into the culture medium. Examples of suitable signal sequences which can be used for the secretion are the signal sequences of alpha-mating factor, of alpha-amylase, of glucoamylase or of invertase.

However, besides E. coli and yeasts, it is also possible to use many other prokaryotic and eukaryotic expression/secretion systems for the preparation of rec. aprotinin variants, such as, for example, Bacilli, Staphylococci or Aspergilli.

As the abovementioned examples show, the expression of aprotinin muteins in various prokaryotic and eukaryotic systems is the state of the art.

It is advantageous in this connection, with a view to preparation on the industrial scale, for the aprotinin variants to be obtained not in a form accumulated within a cell but, by utilization of the secretion mechanisms intrinsic to the system, as active substances exported into the fermentation medium.

When yeast systems are used, for this purpose signal sequences of secretory yeast proteins, such as, for example, of alpha-amylase, of glucoamylase, of invertase or of alpha-mating factor, are fused by genetic engineering to the N terminus of the aprotinin variants.

The enzymatic cleavage of the signal peptide of the N terminus of the aprotinin variants takes place on membrane transfer by an enzyme which is intrinsic to yeast and which recognizes a specific cleavage sequence (at the C terminus of the signal peptide) (see Review Article R. C. Das and J. L. Schultz, Biotechn. Progress 3, 43–48, 1987).

However, it has emerged in the case of the rec. aprotinin variants with the natural N-terminal amino acid sequence "Arg-Pro-Asp" which are expressed in yeasts that, owing to incorrect cleavage off, of the abovementioned signal peptides, the secreted material has variable N-terminal additions of amino acid of the various fused signal peptides. A uniformly and correctly processed secretion product suitable for purification is not found.

The partial or complete faulty processing of secretion products is also described in the literature for other heterologous proteins expressed as fusion products with secretory signal sequences intrinsic to yeasts (R. C. Das and J. L. Schultz, Biotechn. Progress 3, 43–48, 1987; P. J. Barr et al., J. Biol. Chem. 263, 16478–16478, 1988).

SUMMARY OF THE INVENTION

Surprisingly, it has now been found that aprotinin variants which have been modified by genetic engineering and which, for example, have a deletion of the acid proline in position 2 (De Pro2) or which have an N-terminal addition of Ala-(-2)-Gln-(-1) are, to a high percentage, correctly processed in yeast.

Thus the present invention relates to rec. aprotinin or aprotinin variants with a deletion of the amino acid proline in position 2 or an addition of alanine-(-2)-glutamine-(-1). The aprotinin can be of human or animal origin.

Very particularly preferred aprotinin variants are from the group comprising
De Pro2-Val-15-Leu-17,
De Pro2-Val-15-Leu-17-Arg-19,
Ala(-2)-Gln(-1)-Val15-Leu-17,
Ala(-2)-Gln(-1)-Val15-Leu17-Arg-19,
De Pro2-Arg-15,
De Pro2-Arg-15-Ala-17,
Ala(-2)-Gln(-1)-Arg-15,
Ala(-2)-Gln(-1)-Arg-15-Ala-17

The present invention also relates to medicaments containing one or more of the aprotinins described above in combination with a pharmaceutically acceptable carrier.

Preferred aprotinins have, in addition to the above-mentioned exchanges, other exchanges of amino acids in one or more of positions 12, 13, 14, 15, 16, 17, 18, 19, 34, 36, 37, 38, 39, 41, 42 and 52. More details on the exchanges and the amino acids which can be present in each of the positions are to be found in European Patent Applications EP 238,993, 297,362 and 307,592.

DETAILED DESCRIPTION OF THE INVENTION

The examples which follow describe the genetically engineered construction of rec. aprotinin muteins which have N-terminal amino acid sequences which are modified compared with natural aprotinin. Furthermore, the expression of these aprotinin muteins in yeast as fusion product with the alpha-mating factor pre-prosequence, and the purification of the processed secretion products, are described by way of example. The predominantly uniform N-terminal processing of the isolated aprotinin variants and the inhibitory properties thereof are likewise shown.

Methods

Enzymes and standard techniques

The enzymes for molecular genetic experiments were obtained from Boehringer Mannheim (Federal Republic of Germany), Gibco-BRL (U.S.A.) and Pharmacia (Sweden).

The standard techniques for molecular genetic experiments such as, for example, isolation of plasmid DNA from E. coli, isolation and ligation of DNA fragments for cloning experiments with various enzymes are described in Maniatis et al., Molecular Cloning, Cold Spring Harbor (1982).

DNA synthesis

The DNA blocks required for the preparation of the aprotinin variants and DNA primers (for directed mutagenesis) were prepared with the Applied Biosystems 380 A DNA synthesizer. The deprotected DNA oligonucleotides were routinely purified by denaturing polyacrylamide gel electrophoresis or as trityl derivatives by high-pressure liquid chromatography (HPLC).

Directed mutagenesis

The directed mutagenesis of specific amino acid codons or gene sections is carried out by the method of Eckstein (J. W. Taylor, J. Ott and F. Eckstein, Nucl. Acids Res. 13, 8764–8785) using the mutagenesis kit from Amersham-Buchler (Order No. RPN. 2322).

DNA sequencing

To check the DNA sequences of gene and vector constructs, single-stranded DNA subcloned into M13 vectors was sequenced by the method of Sanger (F. Sanger, et. al., PNAS 74, 5463–5467, 1977). Double-stranded DNA was sequenced by the method of M. Hattori and Y. Sakahi (Anal. Biochem. 152, 232–238, 1986).

Transformation of S. cerevisiae 100 ml of a suspension of yeast cells of the strain SC106 (MAT-alpha, hom3, gal2, his6, ura3; strain S2207A, Yeast Genetics Stock Center, University of California Berkeley, Calif. 94720, U.S.A., with a cell concentration of $2 \times 10^7$/ml were centrifuged; the cell sediment was washed once with 5 ml of TE buffer (10 mM Tris$\times$HCl, pH 7.5, 1 mM EDTA) and then with 5 ml of LiA buffer (0.1M lithium acetate in TE buffer). The cells were then suspended in 1 ml of LiA buffer and incubated at 30° C. for 1 hour.

10 $\mu$l of the plasmid solution (1–5 $\mu$g of DNA) and 15 $\mu$l of a carrier DNA (denatured DNA from herring sperm, 3 mg/ml) were added to 0.1 ml of cell suspension. Incubation at 30° C. for 30 minutes was followed by addition of 0.7 ml of polypropylene glycol (40% polypropylene glycol 3350 in LiA buffer) and incubation at 30° C. for a further 60 minutes. The cells were then subjected to a heat shock (42° C., 5 minutes) and then centrifuged in an Eppendorf microfuge for 4 seconds. The cell pellet was washed twice with 0.5 ml of TE buffer each time; the cells were then suspended in 0.1 ml of TE buffer and plated out on selective nutrient medium. Transformants were obtained after incubation at 30° C. for 3 days.

Growth of transformants and analysis of secretion products

Transformants were cultivated in SD medium (0.67% yeast nitrogen base without amino acids, 2% D-glucose) supplemented with threonine, methionine and histidine (20 mg/liter in each case) at 30° C. After a sufficient cell density (usually $5 \times 10^9$ cells/ml) had been reached, the cells were centrifuged, and the trypsin- or elastase-inhibiting activity in the culture supernatant was measured.

Fermentation of yeast transformants for the expression of rec. aprotinin variants on the 10-liter scale The following media were used:

| | | |
|---|---|---|
| SD | Bacto yeast nitrogen base glucose | 6.7 g/ltr. |
| | glucose | 20.0 g/ltr. |
| SD2 | Bacto yeast nitrogen base | 6.7 g/ltr. |
| | glucose | 20.0 g/ltr. |
| | KH$_2$PO$_4$ | 6.7 g/ltr. |
| SC6 | Difco yeast extract | 20.0 g/ltr. |
| | KH$_2$PO$_4$ | 1.4 g/ltr. |
| | (NH$_4$)$_2$SO$_4$ | 2.0 g/ltr. |
| | MgSO$_4$ $\times$ 7 H$_2$O | 0.25 g/ltr. |
| | Antifoam SAG 471 (Union carbide) | 0.1 ml/ltr. |

The components were dissolved in deionized water, and the pH was adjusted to 5.5. The nutrient solutions were sterilized at 121° C. for 20 minutes. Glucose was dissolved in 1/5 of the necessary volume of deionized water, sterilized separately and, after cooling, combined with the nutrient solution.

Stock cultures:

The yeast transformants were maintained on SD plates (SD medium +2% agar) in a refrigerator for up to 4 weeks. Long-term storage was in liquid nitrogen.

Precultures:

Precultures were prepared in SD2 nutrient solution in 1-liter shaken flasks (volume of contents: 100 ml). The flasks were inoculated with a single colony from the SD stock plate and incubated at 28° C. in a shaker at 280 rpm for 2-3 days. (Diameter of shaker orbit: 2.5 or 5.0 cm).

10-Liter fermentation:

10-Liter fermenters were inoculated with the cell sediment from a 1.0-liter preculture suspended in about 200 ml of preculture medium. The fermentation conditions were: SC6 nutrient solution, 28° C., stirrer speed 600 rpm, aeration rate 0.5 vvm, pH control with 2.5N NaOH and 2.5N $H_2SO_4$.

Feeding:

The cultures were fed continuously with glucose and once a day with Difco yeast extract.

Glucose solution:

500 g of glucose in a total volume of 1000 ml; feeding started 4 hours after innoculation at a rate of 0.02 ml/liter×minute, increased to 0.1 ml/liter×minute after 10-20 hours. The glucose introduction rate was chosen so that the respiratory quotient did not rise much above 1.

Difco yeast extract: Yeast extract was added once a day in an amount of 5 g/liter. The yeast extract was prepared as a suspension in deionized water.

Glucose and yeast extract solutions were sterilized at 121° C. for 20 minutes.

After a fermentation time of 96 hours under the stated conditions a cell dry weight of about 30 g/ liter was reached. The yield of product which was achieved was 6 g/liter.

Polyacrylamide gel electrophoresis

Proteins were usually detected by SDS polyacrylamide gel electrophoresis (Laemmli Nature 277, 680, 1970) and staining with Coomassie Brilliant Blue.

Amino acid analysis

About 1 nmol of protein was incubated in the presence of 200 μl of 6M HCl, 0.05% β-mercaptoethanol at 110° C. under vacuum for 22 hours. The hydrolysates were dried, dissolved in 150 μl of 0.2M sodium citrate buffer pH 2.2 and filtered. The amino acid analysis was carried out in a Biotronic LC 5000 amino acid analyzer with fluorescence detector and Shimadzu C-R2AX integrator. The amino acids were quantified after reaction with phthalaldehyde as described in the literature (Benson & Hare, Proc. Natl. Acad. Sci. USA 72, 619, 1975).

Amino acid sequencing 1-2 nmol of protein were dissolved in 30 μl of trifluoroacetic acid and then applied to Polybrene-treated glass fiber filters and sequenced in a gas phase sequenator (Applied Biosystems) by the method of Hewick et al. (J. Biol. Chem. 256, 7990, 1981). Phenylthiohydantoin derivatives were separated and analyzed using a cyano HPLC column (DuPont) as described by Beyreuther et al., Modern Methods in Protein Chemistry, 303-325, Walter de Gruyter, Berlin (1983) and using a Waters HPLC system.

Trypsin inhibition assay

The trypsin activity was determined by the method of Geiger and Fritz, Methods of Enzymatic Analysis, Vol.V 3rd. ed., Bergmeyer (ed), Verlag Chemie, Weinheim (1984), p. 121 with benzoyl-L-arginine p-nitroanilide as substrate. The liberated p-nitroaniline was measured in a spectrophotometer at 405 nm. Enzyme and inhibitor had been preincubated for 15 minutes before the addition of the substrate.

Elastase inhibition assay

Human leucocyte elastase was obtained from Elastin Products Company, Inc. P.O. Box 147, Pacific, Miss. 63069/U.S.A. The substrate used was MeOSuc-Ala-Ala-Pro-Val-pNA (Bachem, Bubendorf/Switzerland). The assay conditions are indicated in Table 3. In general, the inhibitor samples were started after dilution with assay buffer and addition of substrate (dissolved in DMSO in a concentration of 0.1M and adjusted with buffer to the concentration of the stock solution), and the liberation of p-nitroaniline from the substrate was followed continuously at 405 nm. 100% values were determined in corresponding assays without inhibitors. The inhibition (in percent) was calculated from the following equation:

TABLE 3

Conditions of the elastase inhibition assay
(Nakajima et al., J. Biol. Chem. 254, 4027, 1979).

$$\% \text{ Inhibition} = 100 \times \left( 1 - \frac{\text{OD in the presence of inhibitor}}{\text{OD in the absence of inhibitor}} \right)$$

| | |
|---|---|
| Buffer | 0.2M tris/HCl, pH 8.0 + 0.1% Tween 80 |
| Total volume after addition of substrate | 0.65 ml |
| Amount of enzyme/assay | 50 ng |
| Preincubation time at room temperature | 30 minutes |
| Substrate | MeO—Suc—Ala—Ala—Pro—Val—pNA |
| Stock solution | 0.065M |
| Amount/assay | 0.1 ml |
| Assay temperature | 30° C. |

EXAMPLE 1

Construction and cloning of the genes for Val-15-Leu-17-DePro2-Val-15-Leu-17-, DePro2-Arg-15-, DePro2-Val-15-Leu-17-Arg-19- and DePro2-Arg-15-Ala-17-aprotinin A derivative of the E. coli-yeast shuttle vector pMT 15 (FIG. 1) was used for cloning aprotinin muteins in yeast.

The vector pMT 15 contains the ampicillin-resistance gene as selective marker for E. coli and a URA3 gene fragment for yeast. Used for replication in E. coli and yeast was the Col E1 origin from pBR 322 and a DNA segment of the B form of the 2μ plasmid from yeast. For the expression of heterologous genes, the MAT 1-alpha promoter and the coding region for the N-terminal prepro-sequence of alpha-factor precursor protein was incorporated in the form of an Eco RI - Hind III fragment from the plasmid pCY 17 (Korjan and Herskowitz, Cell 30, 933, 1982).

Downstream from the alpha-factor pre-pro-sequence, the vector pMT 15 contains a Bam HI-Sal I fragment of the URA3 gene from yeast with a transcription terminator function (Yarger et al., Mol. Cell. Biol. 8, 1095, 1986).

The 235 bp PstI-Hind III fragment of pMT 15 which carries the coding region of the alpha-factor pre-prosequence was cloned into the vector M13 mp18 and subjected to directed mutagenesis using the oligonucleotide primer 5'-GAA-GAA GGG GTA TTG GAT AAA AGA-3'. The result of the mutagenesis was alteration of the serine codon in pos. 81 of the alpha-factor pre-prosequence from TCT to AGC, which generated a new Hind III restriction cleavage site (FIG. 2). The truncated 213 pb PstI-Hind III fragment was used to replace the 235 bp PstI-Hind III fragment in pMT 15. The plasmid modified in this way was called pS 580; it contains as KEX2 processing site the coding sequence for Lys-Arg in place of Lys-Arg-Glu-Ala-Glu-Ala (FIG. 3).

Used for the fusion with the alpha-factor pre-prosequence in pS 580 was a synthetic Val-15-Leu-17-aprotinin gene which was extended at the 5' end by the last five codons of the alpha-factor pre-pro-sequence up to the Hind III cleavage site in pS 580 (FIG. 4).

The modified Val-15-Leu-17-aprotinin gene was incorporated into the opened Hind III-BamHI cleavage site of pS 580. In this way the 3' end of the alpha-factor pre-pro-sequence was reconstituted with the Lys-Arg processing site, and a reading-frame fusion with the Val-15-Leu-17-aprotinin gene was generated (FIG. 5).

The pS 580 derivative was called pS 604.

To eliminate the amino acid proline position 2 of Val-15-Leu-17-aprotinin, the aprotinin mutein which was fused at the 5' end to the pre-pro-sequence of alpha-factor was isolated as Hind III-Bam-HI cassette from pS 604 and cloned in the mutagenesis vector M13-mp18.

To delete the proline codon in position 2, the following synthetic mutagenesis primer was used in the first mutagenesis cycle: 5'-AGC TTG GAT AAA AGA CGT GAC TTC TGC CTC GAG CCG CCG TAC ACT GGG CC-3'.

The deletion of the proline codon in position 2 of the Val-15-Leu-17 aprotinin gene was verified by DNA sequencing.

To construct the DePro2-Arg-15-aprotinin gene, the DePro2-Val-15-Leu-17-aprotinin gene cloned in the M13-mp18 mutagenesis vector was subjected to a second mutagenesis cycle.

The following mutagenesis primer was used for the molecular genetic exchange of the codons for position 15 and position 17:

5'-T GGG CCC TGC AGA GCT CGT ATC ATC CGT T-3'
                     Arg        Arg

Replacement of Val-15 by Arg-15 and Leu-17 by Arg-17 was confirmed by DNA sequencing.

Subsequently both rec. aprotinin muteins were fused to the alpha-factor pre-pro-sequence by incorporation into the Hind III-Bam HI cleavage sites of the shuttle vector pS 580. The pS 580 derivatives were called pS 707 (contains DePro2-Val-15-Leu-17-aprotinin) and pA 202 (contains DePro2-Arg-15-aprotinin).

The muteins DePro2-Val-15-Leu-17-Arg-19-aprotinin (vector pS773) and DePro2-Arg-15-Ala-17-aprotinin (vector pA206) were constructed and cloned in the manner described above.

EXAMPLE 2

Construction of the genes for
Ala(-2)-Gln(-1)-Val-15-Leu-17-,
Ala(-2)-Gln(-1)-Arg-15,
Ala(-2)-Gln(-1)-Val-15-Leu-17-Arg-19-and
Ala(-2)-Gln(-1)-Arg-15-Ala-17-aprotinin For the genetically engineered addition of the dipeptide Ala-Gln onto the N terminus of the above-mentioned aprotinin muteins, the genes for DePro2-Val-15-Leu-17-aprotinin and DePro2-Arg-15-aprotinin cloned in the M13 mutagenesis vector were subjected to another mutagenesis cycle using the following DNA primer:

5'-AGC TTG GAT AAA AGA GCT CAA CGT CCG GAC TTC TGC C-3'
                               Ala  Gln

The DNA sequence of the two aprotinin muteins modified at the 5' terminus was confirmed by DNA sequencing.

The Ala(-2)-Gln(-1)-Val-15-Leu-17-aprotinin gene and Ala(-2)-Gln(-1)-Arg-15-aprotinin gene were cloned into the yeast shuttle vector pS 580 in analogy to the processes described in Example 1.

The pS 580 derivatives with the cloned aprotinin muteins Ala(-2)-Gln(-1)-Val-15-Leu-17-aprotinin and Ala-(-2)-Gln(-1)-Arg-15-aprotinin were called ps 744 and pA 204, respectively.

The muteins Ala(-2)-Gln(-1)-Val-15-Leu-17-Arg-19-aprotinin (vector pS774) and Ala(-2)-Gln(-1)-Arg-15-Ala-17-aprotinin (vector pA 207) were constructed and cloned in the manner described above.

EXAMPLE 3

Expression of the rec. aprotinin variants in yeast

The yeast strain SC 106 was transformed with the plasmid vectors pS 604, pS 707, pS 744, pS 773, pS 774, pA 202, pA. 204 and pA 207 by the method described above.

The URA 3+ yeast transformants were isolated and cultivated under inducing conditions (see above). To measure the yield, the culture supernatants were tested for elastase-inhibiting activity in the case where the aprotinin muteins to be expressed had valine in position 15 and leucine in position 17. In the case where the aprotinin muteins to be expressed had arginine in position 15, the abovementioned trypsin inhibition assay was carried out. Subsequently, the expression products of the aprotinin muteins secreted in the 10-liter fermenter were purified and characterized.

EXAMPLE 4

Purification of the rec. aprotinin variants

Fermentation broths from 10-liter batches were centrifuged at 9000 rpm (15-30 minutes). The supernatants were filtered through various filters (8 - 0.2 μm), diluted with water to a conductivity of 7.5 mS and adjusted to pH 3 with citric acid. The samples which had been pretreated in this way were mixed with 100-200 ml of S-Sepharose Fast Flow (Pharmacia) in 50 mM sodium citrate pH 3 and stirred for 30-60 minutes. The gel was subsequently washed with 1-5 liters of 50 mM sodium citrate pH 3, 50 mM TRIS HCl pH 9 and finally 20 mM HEPES pH 6. The washed gel was transferred into a suitable column and eluted and fractionated in a BIO-PILOT system (Pharmacia) with a gradient between 0 and 1M sodium chloride in 20 mM HEPES pH 6. After determination of the inhibitory activity in the inhibition assay with human leucocyte elastase or bovine trypsin, the appropriate fractions were collected and concentrated in a rotary evaporator.

This material was further purified by gel filtration on Sephadex G-50 superfine (Pharmacia) and chromatography on S-Sepharose Fast Flow or S-Sepharose HP or Mono S (Pharmacia) in 20 mM HEPES pH 6. A gradient between 0 and 1M NaCl was used for elution from S-Sepharose. Fractions were checked by gel electrophoresis and appropriate inhibition assays. Fractions with inhibitory activity were collected, dialyzed against 0.1M $NH_4HCO_3$ and freeze-dried (FIG. 6).

Yields of 20-40% based on the amount of inhibitors present in the fermentation batch were typically obtained.

EXAMPLE 5

Characterization of the inhibitors obtained as in Example 4

The lyophilizates were initially characterized by amino acid analysis (FIG. 7) and N-terminal sequencing (Applied Biosystems Sequenator) (FIG. 8).

In the case of Val-15-Leu-17-aprotinin, no secreted material which was correctly cleaved at the N-terminus of this aprotinin variant (correct processing) was found. By contrast, the aprotinin variants which have either the deletion in position 2 or else the N-terminal extention Ala(-2)-Gln(-1) were found with 70-90% of correct N-terminal processing (FIGS. 8 and 9).

In addition, the kinetics of inhibition were determined with human leucocyte elastase or porcine pancreas kallikrein (FIG. 10). It emerged from this that the changes at the N terminus have no effect whatever on the inhibitory properties.

BRIEF DESCRIPTION OF THE DRAWINGS

FIG. 4 depicts the DNA sequence of the synthetic Val-15-Leu-17-aprotinin gene with the DNA sequence of the alpha-factor leader (alpha-factor pre-prosequence) extended at the 5' end up to the Hind III cleavage site. The cleavage site of the KEX2 yeast enzyme in the amino acid sequence is marked.

FIG. 7 depicts amino acid analyses of some selected DePro-2, and Ala-(-2)-Gln-(-1) variants.

FIG. 8 depicts an N-terminal sequence analysis of selected DePro-2 and Ala-(-2)-Gln-(-1) variants.

FIG. 9 is a chart depicting the results of processing of some DePro-2 and Ala-(-2)-Gln-(-1) variants by the KEX2 protease.

FIG. 10 is a chart depicting inhibitor constants of DePro-2 and Ala-(-2)-Gln(-1) variants.

Figure 1:
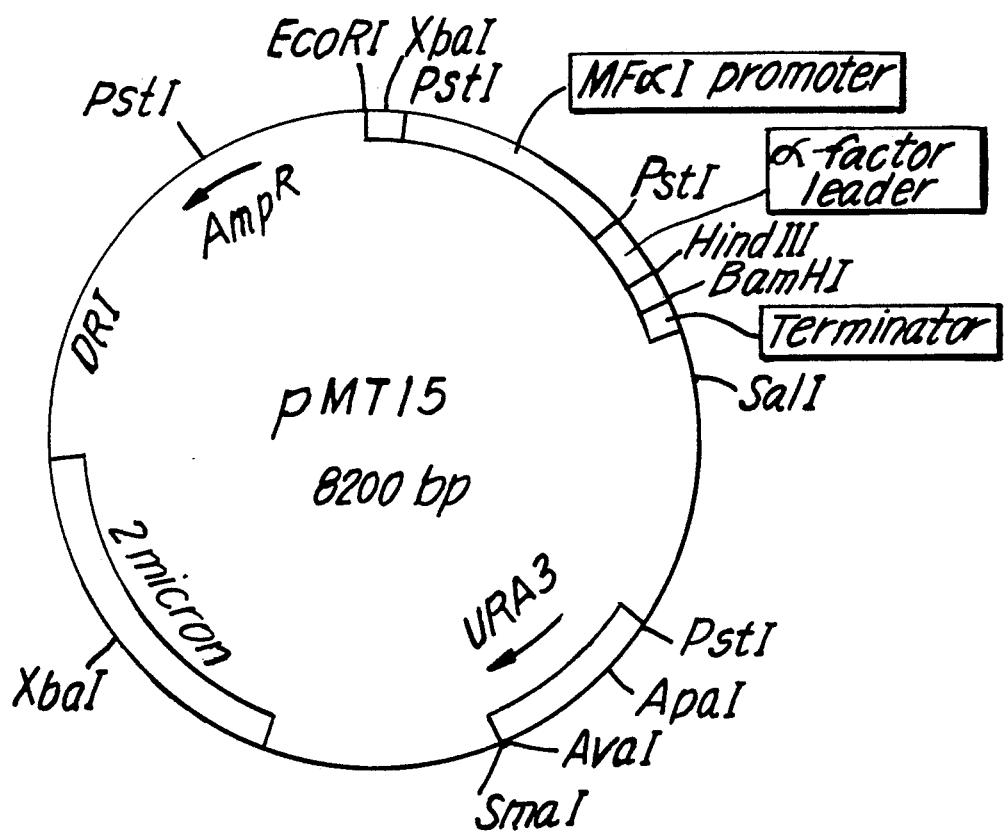
FIG. 1 is a restriction map of the E. coli-yeast shuttle vector pMT 15. The DNA signal sequences essential for gene expression in yeast are boxed.
Figure 2:
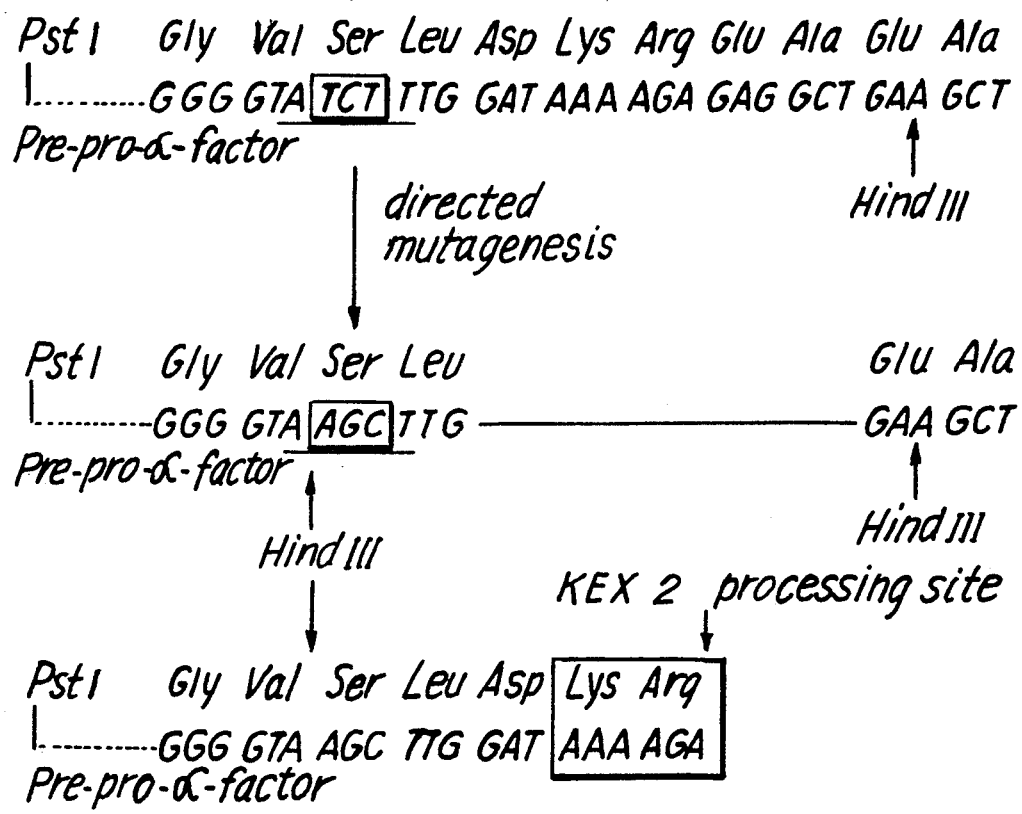
FIG. 2 schematically depicts the genetically engineered introduction of a new Hind III cleavage site into the pre-pro-alpha-factor sequence. The Hind III recognition sequence was generated by exchange of the serine codon (TCT to AGC).
Figure 3:
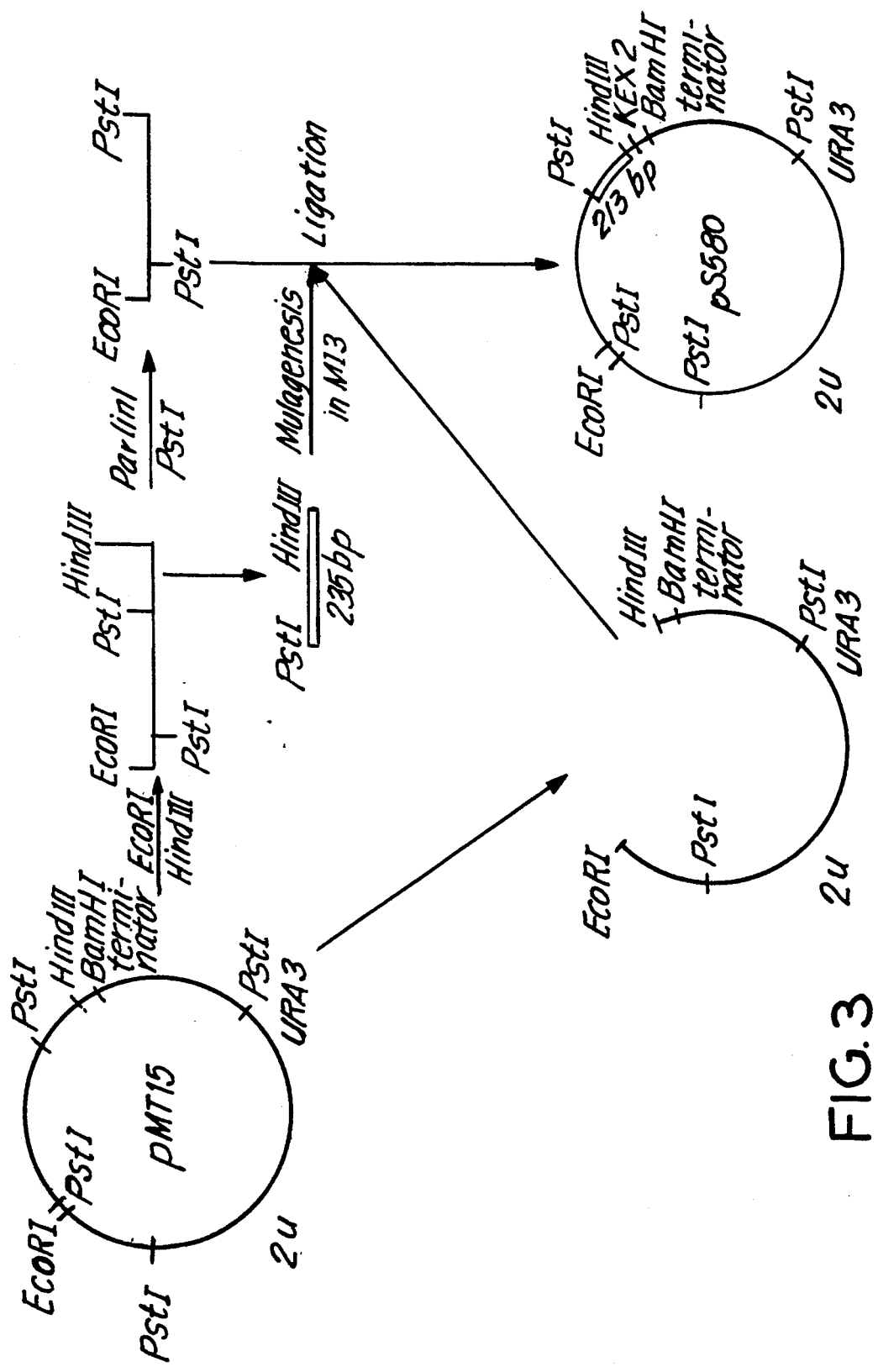
FIG. 3 is a schematic diagram of the construction of the E. coli-yeast shuttle vector pS 580.
Figure 5:
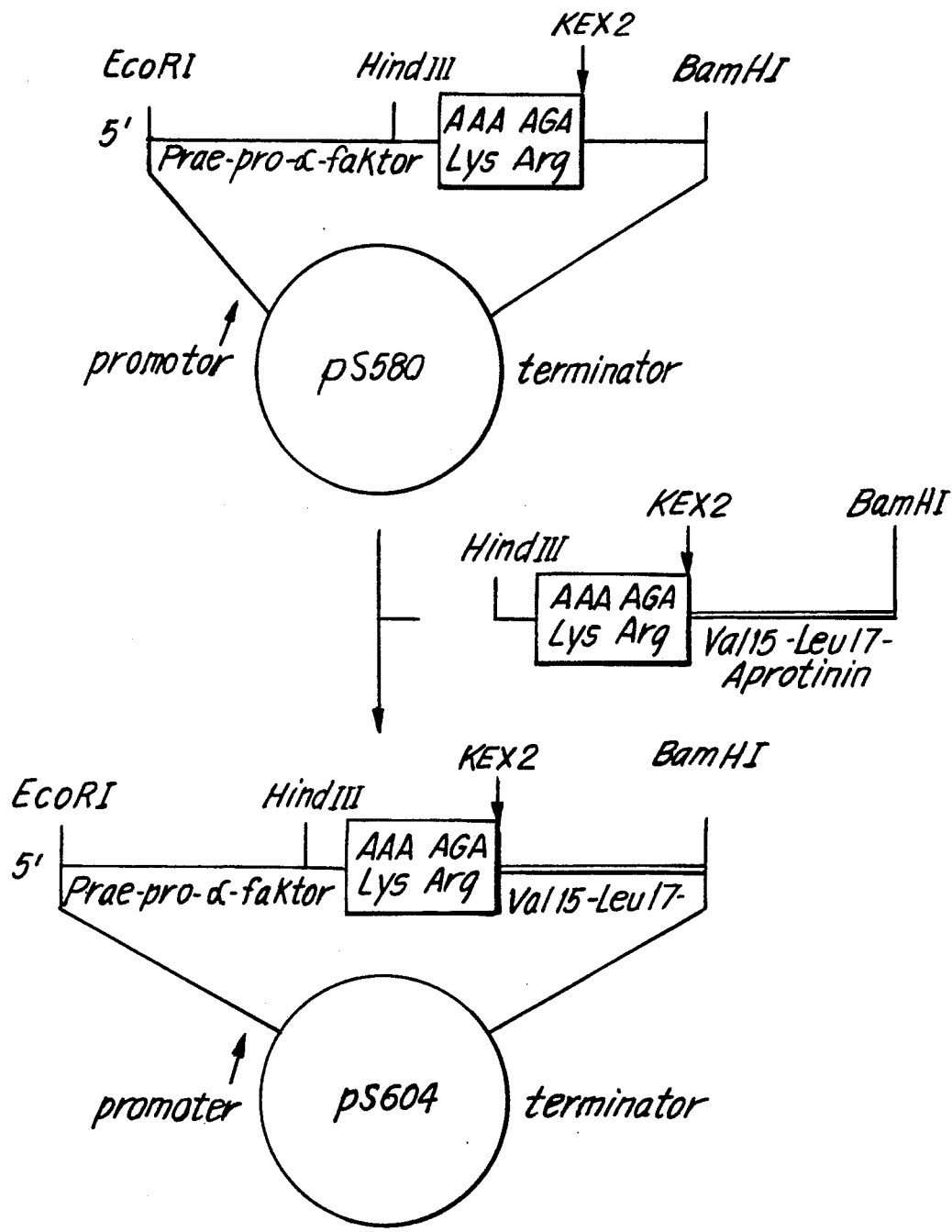
FIG. 5 is a schematic diagram of the construction of the E. coli-yeast shuttle vector pS 604.
Figure 6:
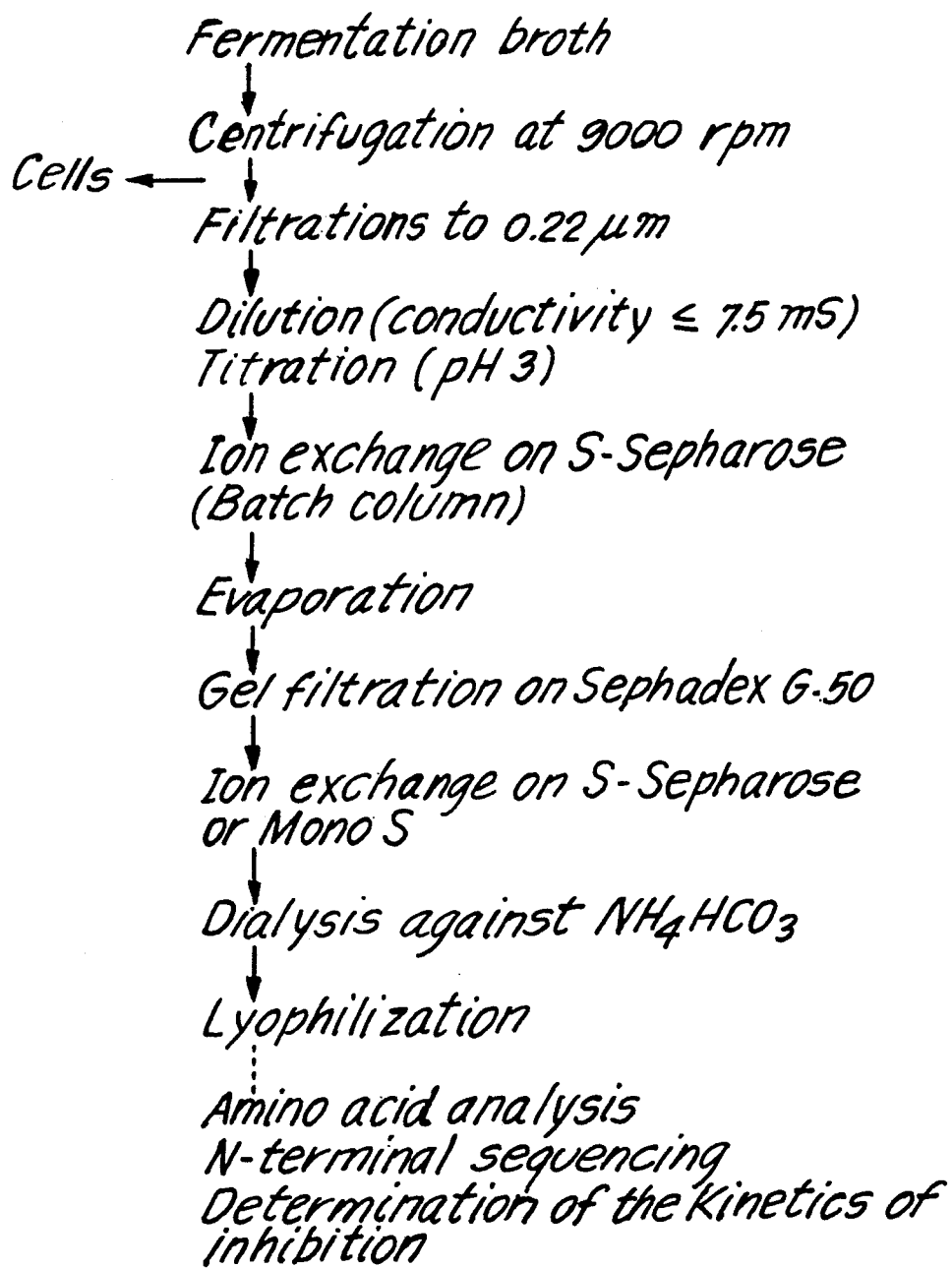
FIG. 6 is a flow diagram of the purification of aprotinin variants from S. cerevisiae fermentation supernatants.

It will be appreciated that the instant specification is set forth by way of illustration and not limitation and that various modifications and changes may be made without departing from the spirit and scope of the present invention.

What is claimed is:

1. An aprotinin with a deletion of the amino acid proline in position 2 or an N-terminal addition of alanine-(-2)-glutamine-(-1).

2. An aprotinin according to claim 1 of human or animal origin.

3. An aprotinin according to claim 1 with additional variations in one or more of positions 15, 16, 17, 18, 19, 34, 39, 41, 42 and 52.

4. An aprotinin according to claim 1, wherein the aprotinin is a variant selected from the group consisting of
DePro-2-Val-15-Leu-17,
DePro-2-Val-15-Leu-17-Arg19,
Ala(-2)-Gln(-1)-Val-15-Leu-17,
Ala(-2)-Gln(-1)-Val-15-Leu-17-Arg-19,
DePro-2-Arg-15,
DePro-2-Arg-15-Ala-17,
Ala(-2)-Gln(-1)-Arg-15, and
Ala(-2)-Gln(-1)-Arg-15-Ala-17.

5. A medicament comprising an effective amount of aprotinin according to claim 1 in combination with a pharmaceutically acceptable carrier.

* * * * *